United States Patent [19]

Gymer et al.

[11] Patent Number: 4,661,507
[45] Date of Patent: Apr. 28, 1987

[54] ANTIFUNGAL S-ETHERS OF 2-ARYL-3-MERCAPTO-1-(1H-1,2,4-TRIAZOL-1-YL) PROPAN-2-OLS AND CORRESPONDING SULFOXIDES AND SULFONES

[75] Inventors: Geoffrey E. Gymer; Kenneth Richardson, both of Canterbury, Great Britain

[73] Assignee: Pfizer Inc., New York, N.Y.

[21] Appl. No.: 645,143

[22] Filed: Aug. 28, 1984

Related U.S. Application Data

[63] Continuation-in-part of Ser. No. 479,524, Mar. 28, 1983, abandoned.

[30] Foreign Application Priority Data

Apr. 1, 1982 [GB] United Kingdom ............... 8209602

[51] Int. Cl.⁴ .................... C07D 249/08; A61K 31/41
[52] U.S. Cl. ..................................... 514/383; 548/262
[58] Field of Search ......................... 548/262; 514/383

[56] References Cited

FOREIGN PATENT DOCUMENTS 0054974  6/1982  European Pat. Off. ............ 548/341
0061835 10/1982  European Pat. Off. ............ 548/262
2908378  9/1980  Fed. Rep. of Germany ...... 514/383
3018865 11/1981  Fed. Rep. of Germany ...... 548/262
2103210  2/1983  United Kingdom ................ 548/262

Primary Examiner—Glennon H. Hollrah
Assistant Examiner—D. Dinner
Attorney, Agent, or Firm—Charles J. Knuth; Albert E. Frost; Peter C. Richardson

[57] ABSTRACT

Compounds of the general formula:

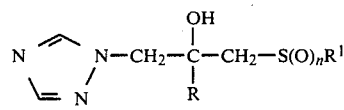

wherein R is naphthyl, biphenylyl, phenyl or substituted phenyl; n is 0, 1 or 2; and $R^1$ is H, $C_{1-6}$ alkyl, $C_{3-7}$ cycloalkyl, $C_{2-4}$ alkanoyl, or $C_{1-2}$ alkyl substituted by $C_{2-4}$ alkenyl with the provisos that when $R^1$ is H or $C_{2-4}$ alkanoyl, n is 0; and when n is 2, $R^1$ is $C_{1-3}$ alkyl; and their pharmaceutically acceptable salts are antifungal agents useful in combatting fungal infections in animals, including humans.

9 Claims, No Drawings

ANTIFUNGAL S-ETHERS OF 2-ARYL-3-MERCAPTO-1-(1H-1,2,4-TRIAZOL-1-YL) PROPAN-2-OLS AND CORRESPONDING SULFOXIDES AND SULFONES

CROSS-REFERENCE TO RELATED APPLICATION

This application is a continuation-in-part of co-pending application Ser. No. 479,524 now abandoned, filed Mar. 28, 1983.

BACKGROUND OF THE INVENTION

This invention relates to novel triazole derivatives which have antifungal activity and are useful in the treatment of fungal infections in animals, including humans.

European Patent Application No. 82,300,888.3, published Oct. 6, 1982 as Publication No. 0,061,835, broadly describes a large series of S- and O-ethers of 2-aryl-3-mercapto (or 3-hydroxy)-1-(1H-1,2,4-triazol-1-yl)propan-2-ols, and of the corresponding sulfoxides and sulfones of said mercapto derivatives, as antifungal agents.

Related S-ethers of 2-aryl-3-mercapto-1-(1H-1,2,4-triazol-1-yl)propan-2-ols as antifungal agents are described in concurrently filed U.S. patent applications of Richardson and Whittle, entitled "Triazole Antifungal Agents"; and of Richardson, Whittle and Cooper, entitled "Antifungal S-Arylmethyl- and S-Heterocyclylmethyl Ethers of 2-Aryl-3-Mercapto-1-(1H-1,2,4-Triazol-1-yl)Propan-2-Ols", said applications being Ser. Nos. 479,525 and 479,526, now U.S. Pat. No. 4,505,919, filed Mar. 28, 1983.

SUMMARY OF THE INVENTION

According to the invention, there are provided compounds of the formula:

$$N\overset{\frown}{=}N-CH_2-\underset{R}{\overset{OH}{\underset{|}{C}}}-CH_2-\underset{(O)_n}{\overset{||}{S}}-R^1 \quad \text{I}$$

and their O-esters and O-ethers;
wherein
R is naphthyl, biphenylyl, phenyl, or substituted phenyl;
$R^1$ is H, $C_1-C_6$ alkyl, $C_3-C_7$ cycloalkyl, $C_2-C_4$ alkanoyl, or $C_1-C_2$ alkyl substituted by $C_2-C_4$ alkenyl; and
n is 0, 1 or 2, with the provisos and when
n is 2, $R^1$ is $C_{1-3}$ alkyl; that when $R^1$ is H or $C_2-C_4$ alkanoyl, n is 0;
and their pharmaceutically acceptable salts.

The O-ethers of the alcohols of the formula (I) include, for example, the $C_1-C_6$ alkyl, $C_2-C_4$ alkenyl, $C_2-C_4$ alkynyl, aryl (e.g. phenyl) and aralkyl (e.g. benzyl optionally ring substituted by halo, $C_1-C_4$ alkyl or $C_1-C_4$ alkoxy) ethers.

The O-esters of the alcohols of the formula (I) include, for example, the $C_2-C_4$ alkanoyl and aroyl (e.g. benzoyl, optionally substituted by halo, $C_1-C_4$ alkyl or $C_1-C_4$ alkoxy) esters.

The preferred O-ester is the acetyl ester.

"Substituted phenyl" is preferably phenyl substituted by 1 to 3 substituents, more preferably 1 or 2 substituents, each independently selected from halo, $CF_3$, $C_1-C_4$ alkyl and $C_1-C_4$ alkoxy.

More preferably, "substituted phenyl" is phenyl substituted by 1 to 3 substituents, especially 1 or 2 substituents, each independently selected from halo or $CF_3$. The most preferred individual groups represented by R are 4-fluorophenyl, 4-chlorophenyl, 4-bromophenyl, 4-iodophenyl, 4-trifluoromethylphenyl, 2-chlorophenyl, 2,4-dichlorophenyl, 2,4-difluorophenyl, 2,5-difluorophenyl, 2-fluoro-4-chlorophenyl, 2,4,6-trifluorophenyl and 4-bromo-2,5-difluorophenyl.

"Halo" means F, Cl, Br or I.

Where appropriate, alkyl, alkoxy, alkenyl and alkynyl groups can be straight or branched chain.

The preferred biphenylyl group is p-biphenylyl, of the formula:

$$\langle\!\!\!\bigcirc\!\!\!\rangle\!\!-\!\!\langle\!\!\!\bigcirc\!\!\!\rangle\!\!-$$

$R^1$ is preferably H, $C_1-C_4$ alkyl, $C_3-C_6$ cycloalkyl (most preferably cyclohexyl), allyl, or acetyl. $R^1$ is most preferably $CH_3$.

R is most preferably 2,4-dichlorophenyl, 2,4-difluorophenyl or 2-chlorophenyl.

The most preferred compound has the formula:

$$N\overset{\frown}{=}N-CH_2-\underset{\underset{\underset{Cl}{\bigcirc}}{\overset{Cl}{|}}}{\overset{OH}{\underset{|}{C}}}-CH_2SO_2CH_3.$$

The invention also provides a pharmaceutical composition comprising a compound of the formula (I), or an O-ester, O-ether or pharmaceutically acceptable salt thereof, together with a pharmaceutically acceptable diluent or carrier.

The invention yet further provides a method of treating a fungal infection in a human being, which comprises administering to the human an effective amount of a compound of the formula (I) or a pharmaceutically acceptable salt thereof.

The invention further provides a compound of the formula (I), or an O-ester, O-ether or a pharmaceutically acceptable salt thereof, for use in treating a fungal infection in a human being.

DETAILED DESCRIPTION OF THE INVENTION

The compounds of the formula (I) can be obtained by a number of different processes:

(1) The compounds of the formula (I) in which n is 0 can be prepared as follows:

$$N\overset{\frown}{=}N-CH_2-\underset{R}{\overset{}{\underset{|}{C}}}\overset{O}{\overset{/\backslash}{\underset{}{-}}}CH_2 + R^1.SH \longrightarrow$$

(II)          (III)

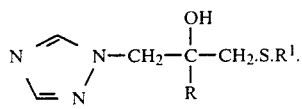

(IA)

It is preferred to carry out the reaction in an organic solvent in the presence of a base, e.g. sodium hydroxide, sodium hydride or potassium carbonate. Preferred base/solvent combinations are NaH/tetrahydrofuran, NaH/DMF and NaOH/dioxan. The reaction is typically achieved by mixing the reactants together in the organic solvent with, if necessary, heating at up to 120° C., until the reaction is complete, generally in 24 hours or less. The product can be isolated and purified by conventional procedures.

When $R^1$ is $C_2$-$C_4$ alkanoyl, a mixture of the compound (IA) and its O-alkanoyl derivative may be formed. These can be separated by chromatography according to known techniques.

The oxiranes (II) can be obtained by conventional methods, typically from the corresponding ketones:

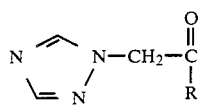

by reacting them in a suitable solvent (e.g. dry dimethylsulphoxide) with dimethyloxosulphonium methylide prepared from trimethylsulphoxonium iodide and either sodium hydride or cetrimide/sodium hydroxide in toluene/water.

The reaction using sodium hydride is typically achieved by adding dry powdered trimethylsulphoxonium iodide to a suspension of sodium hydride in dimethylsulfoxide. After stirring for, say, 30 minutes at room temperature, the ketone is added in an approximately equimolar amount in dimethylsulphoxide. The reaction mixture may be warmed to accelerate the reaction and after several hours at 50°-80° C., the product can be isolated by conventional procedures.

The reaction utilizing cetrimide is typically achieved as follows. The ketone, trimethylsulphoxonium iodide and cetrimide are stirred vigorously in a mixture of toluene and sodium hydroxide solution for about an hour at up to about 100° C. The oxirane product can then be isolated by conventional procedures.

When R is a phenyl group containing no ortho substituent or biphenylyl, the cetrimide route should be used.

The ketones are either known compounds or can be prepared by procedures analogous to those of the prior art. The preparation of 2-(1H-1,2,4-triazol-1-yl)-2',4'-dichloroacetophenone from 2-bromo-2',4'-dichloroacetophenone, 1,2,4-triazole and potassium carbonate is for example, described in Example 1 of British Patent Specification No. 1,512,918, which utilizes acetonitrile as the solvent under reflux for 20 hours. We have found that this type of reaction is generally best carried out in acetone at 0°-20° C., when it is generally complete in a shorter period of time, e.g. 4 hours or less.

(2) Compounds of the formula (I) in which $R^1$ is H (and thus n=0) can be prepared by the deacylation of the corresponding compounds in which $R^1$ is $C_2$-$C_4$ alkanoyl, preferably acetyl. The deacylation is preferably carried out using sodium ethoxide in ethanol, followed by acidification (e.g. with HCl) according to the following procedure:

 (IV)

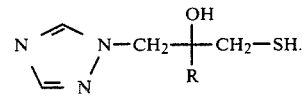

(V)

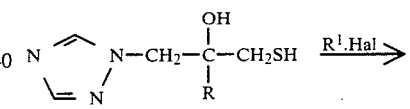

(IB)

The reaction is typically carried out by adding the alkanoyl derivative (IV) dropwise to a stirred and cooled solution of sodium ethoxide in ethanol. After about an hour the resulting mixture is poured into aqueous acid, e.g. 1N hydrochloric acid, followed by neutralization, e.g. by the addition of solid sodium bicarbonate. The thiol product (IB) can again be isolated and purified by conventional procedures.

(3) The compounds of the formula (I) in which n is 0 and $R^1$ is other than H can also be prepared as follows:

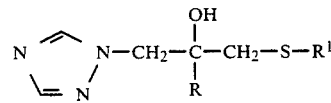

(IB)

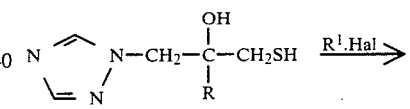

(IC)

[Hal=Cl, Br or I, preferably Br or I].

The reaction is preferably carried out in the presence of a base, e.g. NaOH or $K_2CO_3$. Typically, the thiol (IB), halide and base are stirred together at room temperature in a suitable organic solvent for a few hours. Preferred base/solvent combinations are $K_2CO_3$/acetone and sodium hydroxide/aqueous ethanol. If necessary, the reaction mixture can be heated, e.g. to 70° C., to accelerate the reaction. The product can be isolated and purified by conventional procedures.

(4) The compounds of the formula (I) in which n is 1 (sulphoxides) and 2 (sulphones) can be prepared by the controlled or strong oxidation, respectively, of the corresponding compounds in which n is 0. The compounds in which n is 2 can also be prepared by the oxidation of the compounds in which n is 1.

The preferred oxidizing agent is m-chloroperbenzoic acid: approximately one equivalent should be used to prepare the sulphoxides and an excess to prepare the sulfones.

In a typical procedure involving the preparation of a sulphoxide, the corresponding thio compound is dissolved in a mixture of isopropanol and chloroform (1:1, v/v) and the solution is cooled to below 5° C. in an ice bath. Slightly less than 1 equivalent of m-chloroperbenzoic acid is added in portions over a few minutes. The mixture is then stirred for about 2 hours. If t.l.c. indicates unreacted starting material, a small further quantity of m-chloroperbenzoic acid (to approximately 1 equivalent) is added. As stated hereinafter, the sulphoxides have two asymmetric centers and thus exist in two diastereoisomeric forms. Thus the sulphoxide product of the oxidation, which can be isolated by conventional procedures, will be a mixture of the two diastereoisomers. If desired, the diastereoisomers can be separated by column chromatography, e.g. on silica, since they differ markedly in polarity. The sulphones can be obtained simply by adding excess m-chloroperbenzoic acid to a solution of the crude sulphoxide (or sulphoxides) in e.g. chloforom, and stirring for a few hours, e.g. three hours, at room temperature. Alternatively the sulphones can be prepared by the oxidation of the thio compounds (n=0) using excess m-chloroperbenozic acid.

(5) The ethers can be made by treating an alkali metal salt of the alcohols of the formula (I), e.g. a lithium or sodium salt, with the appropriate halide, e.g. an alkyl, alkenyl, alkynyl, aryl or aralkyl halide. Esters can be made by treating an alkali metal salt of compound (I) with the appropriate acid chloride, bromide or anhydride.

The sulphoxides of the formula (I) have two asymmetric centers, namely the carbon atom bearing the hydroxy group, and the sulphoxide sulphur atom. Consequently the sulphoxides exist in two diastereoisomeric forms, each of which is in fact a racemate consisting of a pair of enantiomers. The two diastereoisomeric forms can be readily separated by column chromatography, since they differ markedly in polarity. Each diastereoisomer can be resolved further into its individual optically active enantiomers by techniques known to those skilled in the art. In some cases, one diastereoisomer may predominate over the other.

The invention includes both diastereoisomers whether resolved or not.

All the compounds of the invention contain at least one chiral center, and the invention includes both resolved and unresolved forms.

Pharmaceutically acceptable acid addition salts of the compounds of the formula (I) are those formed from strong acids which form non-toxic acid addition salts, such as hydrochloric, hydrobromic, sulphuric, oxalic and methanesulphonic acids.

The salts may be obtained by conventional procedures, e.g. by mixing solutions containing equimolar amounts of the free base and desired acid, and the required salt is collected by filtration, if insoluble, or by evaporation of the solvent.

The compounds of the formula (I) and their pharmaceutically acceptable salts are antifungal agents, useful in combatting fungal infections in animals, including humans. For example they are useful in treating topical fungal infections in man caused by, among other organisms, species of Candida, Trichophyton, Microsporum, or Epidermophyton, or in mucosal infections caused by *Candida albicans* (e.g. thrush and vaginal candidiasis). They may also be used systemically in the treatment of systemic fungal infections caused by, for example, *Candida albicans, Cryptococcus neoformans, Aspergillus fumigatus,* Coccidioides, Paracoccidioides, Histoplasma or Blastomyces.

The in vitro evaluation of the antifungal activity of the compounds can be performed by determining the minimum inhibitory concentration (m.i.c.) of the test compounds in a suitable medium at which growth of the particular microorganism fails to occur. In practice, a series of agar plates, each having the test compound incorporated at a particular concentration are inoculated with a standard culture of, for example, *Candida albicans* and each plate is then incubated for 48 hours at 37° C. The plates are then examined for the presence or absence of growth of the fungus and the appropriate m.i.c. value is noted. Other microorganisms used in such tests can include *Cryptococcus neoformans, Aspergillus fumigatus,* Trichophyton spp; Microsporum spp; *Epidermophyton floccosum, Coccidioies immitis,* and *Torulopsis glabrata.*

The in vivo evaluation of the compounds can be carried out at a series of dose levels by intraperitoneal or intravenous injection or by oral administration, to mice which are inoculated with a strain of *Candida albicans.* Activity is based on the survival of a treated group of mice after the death of an untreated group of mice following 48 hours observation. The dose level at which the compound provides 50% protection against the lethal effect of the infection is noted.

For human use, the antifungal compounds of the formula (I) can be administered alone, but will generally be administered in admixture with a pharmaceutical carrier selected with regard to the intended route of administration and standard pharmaceutical practice. For example, they may be administered orally in the form of tablets containing such excipients as starch or lactose, or in capsules or ovules either alone or in admixture with excipients, or in the form of elixirs or suspensions containing flavoring or coloring agents. They may be injected parenterally, for example, intravenously, intramuscularly or subcutaneously. For parenteral administration, they are best used in the form of a sterile aqueous solution which may contain other substances, for example, enough salts or glucose to make the solution isotonic.

For oral or parenteral administration to human patients, the daily dosage level of the antifungal compounds of the formula (I) (and salts, O-esters and O-ethers thereof) will be from 0.1 to 5 mg/kg (in divided doses) when administered by either the oral or parenteral route. Thus tablets or capsules of the compounds can be expected to contain from 5 mg to 0.5 g of active compound for administration singly or two or more at a time as appropriate. The physician in any event will determine the active dosage which will be most suitable for an individual patient and it will vary with the age, weight and response of the particular patient. The above dosages are exemplary of the average case. There can, of course, be individual instances where higher or lower dosage ranges are merited, and such are within the scope of this invention.

Alternatively, the antifungal compounds of formula (I) may be administered in the form of a suppository or pessary, or they may be applied topically in the form of a lotion, solution, cream, ointment or dusting powder.

For example, they may be incorporated into a cream consisting of an aqueous emulsion of polyethylene glycols or liquid paraffin; or they may be incorporated, at a concentration between 1 and 10%, into an ointment consisting of a white wax or white soft paraffin base together with such stabilizers and preservatives as may be required.

The following Examples illustrate the invention.

EXAMPLE 1

Preparation of 3-Cyclohexylthio-2-(2,4-dichlorophenyl)-1-(1H-1,2,4-triazol-1-yl)propan-2-ol, Mesylate Salt

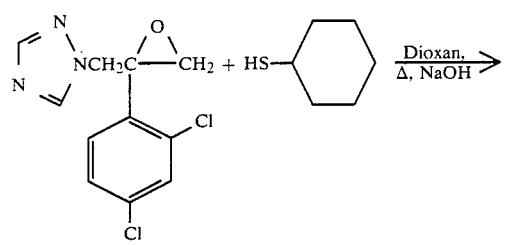

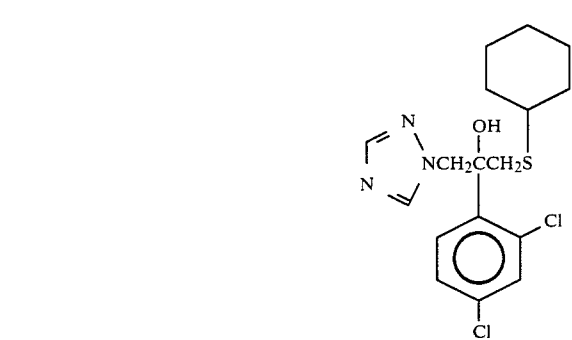

2-(1H-1,2,4-Triazol-1-ylmethyl)-2-(2,4-dichlorophenyl)oxirane (540 mg), cyclohexyl mercaptan (232 mg), 5N aqueous sodium hydroxide (1 drop) and dioxan (20 ml) were mixed together and heated under reflux for two hours. The solution was cooled and then evaporated to dryness. The residue was partitioned between ethyl acetate and saturated aqueous $NaHCO_3$ solution. The organic phase was separated, washed with brine, dried ($MgSO_4$), filtered and evaporated to dryness. The residue was chromatographed on silcia eluting with hexane containing 0–20% ethyl acetate. The product was evaporated to dryness to yield a gum, 754 mg. 130 Mg of the gum in diethyl ether (10 ml) was treated with $CH_3SO_2OH$ (22 μl) to yield the title mesylate salt, yield 139 mg, m.p. 170°–172° C.

Analysis %: Found: C, 45.2; H, 5.6; N. 8.8; $C_{18}H_{21}Cl_2N_3OS.CH_3SO_3H$ requires: C, 44.8; H, 5.2; N, 8.7.

EXAMPLE 2

Preparation of 3-Allylthio-2-(2,4-dichlorophenyl)-1-(1H-1,2,4-triazol-1-yl)propan-2-ol

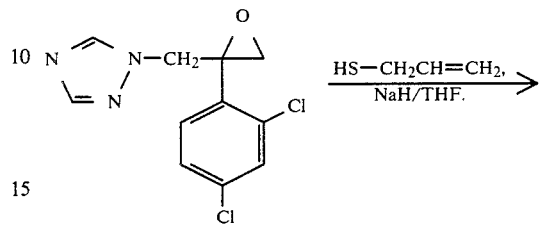

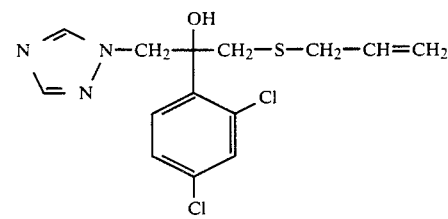

Sodium hydride (0.23 g, 50% dispersion in oil, 1.2 equivalents) was added to a solution of allyl mercaptan (0.465 g, 1.1 equivalents) in dry tetrahydrofuran (20 ml), and stirred until gas evolution ceased. The epoxide (B) (1.08 g), dissolved in dry tetrahydrofuran (10 ml), was added, and the mixture stirred at 45°–50° C. for two hours, then overnight at room temperature (20° C.). Water (100 ml) was added, and the resulting solution extracted with methylene chloride (3×50 ml). The organic extracts were combined, washed with sodium hydroxide solution (2×50 ml, 2N), saturated sodium chloride solution (2×50 ml) and dried ($MgSO_4$). Evaporation yielded a gum, 900 mg, which was chromatographed on silica, eluting with a 5–10% gradient of isopropanol in n-hexane containing a trace of ammonia, to give the title compound, which was recrystallized from cyclohexane, yield 698 mg, m.p. 92°–94° C.

Analysis %: Found: C, 48.8; H, 4.3; N, 12.3; $C_{14}H_{15}Cl_2N_3OS$ requires: C, 48.8; H, 4.4; N, 12.2.

EXAMPLE 3

The following compound, m.p. 75°–6°, was prepared similarly to Example 2, starting from the appropriate epoxide, methanethiol and NaH:

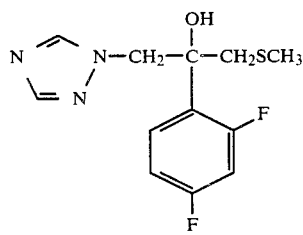

Analysis %: Found C, 50.59; H, 4.63; N, 14.96; Calculated for $C_{12}H_{13}F_2N_3OS$: C, 50.51; H, 4.59; N, 14.73.

EXAMPLE 4

Preparation of
3-Allylsulphinyl-2-(2,4-dichlorophenyl)-1-(1H-1,2,4-triazol-1-yl)propan-2-ol

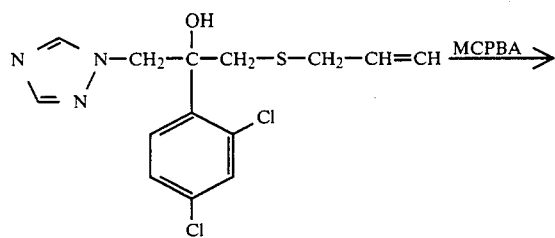

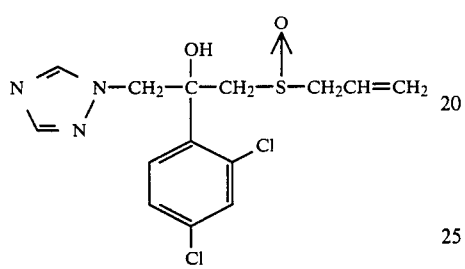

The allylthio product of Example 2 (340 mg) was dissolved in a mixture of isopropanol and chloroform (10 ml, 1:1, v/v) and the solution cooled in an ice bath. when the temperature had fallen to below 5° C., meta-chloroperbenzoic acid (MCPBA) (160 mg, 85% pure, 0.8 equivalents) was added in small portions over five minutes. Stirring was continued for 30 minutes at ice bath temperature, then overnight at room temperature. T.l.c. indicated some starting material remained, so a further portion of metachloroperbenozic acid (40 mg, 0.2 equivalents) was added, and stirring continued for a further hour at room temperature. T.l.c. then indicated no starting material remained, the solution now containing two more polar materials. The reaction mixture was added to a solution of sodium sulphite 2% and sodium carbonate 2% in water (100 ml) and the resulting mixture was extracted with chloroform (3×50 ml). The combined organic extracts were washed with the sulphite/carbonate solution (3×50 ml) and then with water (3×50 ml), dried (MgSO₄) and evaporated to the crude product as a gum, 330 mg. This gum was a mixture of two diastereoisomers.

Chromatography on silica, eluting with 2–5% gradient of isopropanol in methylene chloride containing a trace of ammonia, gave firstly (a) the less polar diastereoisomer, yield 158 mg, m.p. 127°–128° C., Analysis %: Found: C, 46.3; H, 4.2; N, 11.6; $C_{14}H_{15}Cl_2N_3O_2S$ requires: C, 46.6; H, 4.2; N, 11.7.

and secondly (b) the more polar diastereoisomer, which was converted to the oxalate salt with a solution of oxalic acid in ethyl acetate, yield 36 mg, m.p. 61°–63° C.

Analysis %: Found: C, 41.7; H, 3.9; N, 9.1; $C_{14}H_{15}Cl_2N_3O_2S.(COOH)_2.\frac{1}{2}H_2O$ requires: C, 41.8; H, 3.9; N, 9.1.

EXAMPLES 5A AND 5B

The following compound was prepared similarly to the previous Example, starting from the corresponding methylthio compound and MCPBA, and, again, it was isolated in two diastereoisomeric forms:

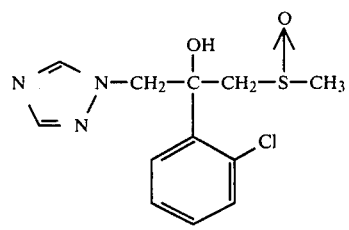

A. Diastereoisomer 1

M.p. 122°–3°

Analysis %: Found: C, 48.06; H, 4.61; N, 14.23; Calculated for $C_{12}H_{14}ClN_3O_2S$: C, 48.08; H, 4.67; N, 14.02.

B. Diastereoisomer 2

M.p. 156°–7°

Analysis %: Found: C, 48.24; H, 4.80; N, 14.18; Calculated for $C_{12}H_{14}ClN_3O_2S$: C, 48.08; H, 4.67; N, 14.02.

EXAMPLES 6-15

In the following Examples, the ethylthio product of Example 8, and the n-butylthio product of Example 11, were prepared similarly to the procedures of Examples 2 and 1, respectively, from appropriate starting materials. The sulphinyl compounds were prepared similarly to the procedure of Example 4 by the controlled oxidation of the corresponding alkylthio or cycloalkylthio compounds followed by chromatography to separate the diastereoisomers: generally the less polar diastereoisomer was the major diastereoisomer in a ratio of about 3:1. Unless otherwise indicated, the compounds were characterized in the free base form.

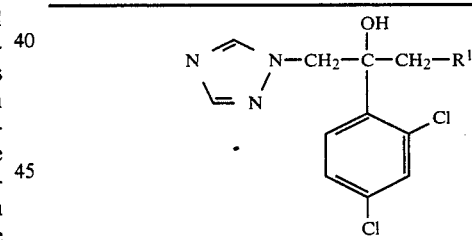

| Example No. | R¹ | Analysis % (or n.m.r.) | m.p. (°C.) |
|---|---|---|---|
| 6 | —S(=O)—CH₃ diastereoisomer 1 | Found: C, 43.4; H, 3.7; N, 12.3 $C_{12}H_{13}Cl_2N_3O_2S$ requires: C, 43.2; H, 3.9; N, 12.6% | 171–173 |
| 7 | —S(=O)—CH₃ diastereoisomer 2 | Found: C, 42.9; H, 3.9; N, 12.5 $C_{12}H_{13}Cl_2N_3O_2S$ requires: C, 43.2; H, 3.9; N, 12.6% | 142–144° |
| 8 | —S—C₂H₅ | Found: C, 47.1; H, 4.3; N, 12.8 $C_{13}H_{15}Cl_2N_3OS$ requires: C, 47.0; H, 4.5; N, 12.7% | 100–103° |

4,661,507

11
-continued

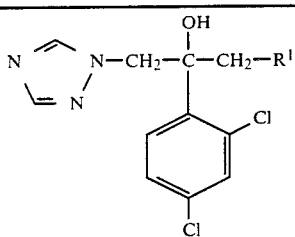

| Example No. | R¹ | Analysis % (or n.m.r.) | m.p. (°C.) |
|---|---|---|---|
| 9 | —S—C₂H₅ (with O double bond up) diastereoisomer 1 | Found: C, 45.1; H, 4.2; N, 12.2<br>C₁₃H₁₅Cl₂N₃O₂S requires: C, 44.8; H, 4.4; N, 12.1% | 155–156° |
| 10 | —S—C₂H₅ (with O double bond up) diastereoisomer 2 | Found: C, 44.4; H, 4.2; N, 12.3<br>C₁₃H₁₅Cl₂N₃O₂S requires: C, 44.8; H, 4.4; N, 12.1% | 147–149° |
| 11 | —S—(CH₂)₃CH₃ | Found: C, 42.4; H, 5.2; N, 9.2<br>C₁₅H₁₉Cl₂N₃OS.CH₃SO₃H requires: C, 42.1; H, 5.0; N, 9.2% | 94–96° (mesylate salt) |
| 12 | —S—(CH₂)₃CH₃ (with O double bond up) diastereoisomer 1 | n.m.r. (CDCl₃): delta = 9.95 (s) 1H; 8.45 (s) 1H; 7.7 (d) 1H, J9Hz; 7.4 (d) 1H, J2Hz; 7.25 (dd) 1H, J9Hz, 2Hz; 5.2 (s) 2H, 4.0 (d) 1H, J14Hz; 3.4 (d) 1H, J14Hz; 2.8 (bs) 5H; 1.5 (m) 4H; 0.9 (m) 3H | gum (mesylate salt) |
| 13 | —S—(CH₂)₃CH₃ (with O double bond up) diastereoisomer 2 | Found: C, 47.8; H, 5.1; N, 11.3<br>C₁₅H₁₉Cl₂N₃O₂S requires: C, 47.9; H, 5.1; N, 11.2% | 127–129° |
| 14 | —S—cyclohexyl (with O double bond up) diastereoisomer 1 | Found: C, 50.7; H, 5.1; N, 10.9<br>C₁₈H₂₁Cl₂N₃O₂S requires: C, 50.7; H, 5.2; N, 10.5% | 142–145° |
| 15 | —S—cyclohexyl (with O double bond up) diastereoisomer 2 | Found: C, 50.5; H, 5.2; N, 10.8<br>C₁₈H₂₁Cl₂N₃O₂S requires: C, 50.7; H, 5.2; N, 10.5% | 136–139° |

EXAMPLE 16

Preparation of 2-(2,4-Dichlorophenyl)-3-mercapto-1-(1H-1,2,4-triazol-1-yl)propan-2-ol 2-(1H-1,2,4-Triazol-1-ylmethyl)-2-(2,4-dichlorophenyl)oxirane 5 g (0.185M) was heated under mild reflux in thioacetic acid (CH₃COSH) (5 ml) for three hours. The mixture was then cooled and added to a mixture of ice-cooled saturated sodium bicarbonate solution (200 ml) and ethyl acetate (200 ml) and the aqueous layer was separated. The organic layer was washed a further four times with ice cooled saturated sodium bicarbonate solution (200 ml in total), dried (MgSO₄) and evaporated to give a red gum which was dissolved in ethanol (20 ml). This solution was added dropwise over 15 minutes to a stirred and ice-cooled solution of sodium ethoxide (3.78 g, 0.0556M) in ethanol (100 ml). After one hour the mixture was poured into 1N hydrochloric acid (100 ml) and this solution was then neutralized by addition of solid sodium bicarbonate. Extraction with methylene chloride (6×50 ml), drying (MgSO₄), and evaporation of the combined extracts gave a gum which was chromatographed on silica, eluting with ethyl acetate, to give after one recrystallization from ethyl acetate/hexane the title compound, yield 2.3 g, m.p. 139°–142.5° C.

Analysis %: Found: C, 43.3; H, 3.7; N, 14.0; Calculated for C₁₁H₁₁Cl₂N₃OS: C, 43.4; H, 3.6; N, 13.8.

EXAMPLE 17

Preparation of 3-Methylthio-2-(2,4-dichlorophenyl)-1-(1H-1,2,4-triazol-1-yl)propan-2-ol

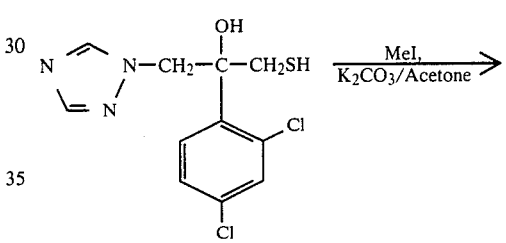

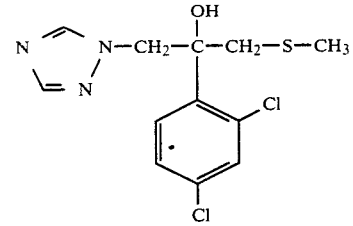

3-Mercapto-2-(2,4-dichlorophenyl)-1-(1H-1,2,4-triazol-1-yl)propan-2-ol (230 mg) (prepared as in the previous Example), potassium carbonate (138 mg, 2.7 equivalents), and methyl iodide (200 mg, 1.9 equivalents) were stirred together in acetone (15 ml) at room temperature for two hours. The acetone was then evaporated under reduced pressure, and the residue triturated with water to give the crude title compound as a solid, 220 mg. This was crystallized from isopropanol to yield the pure title compound, yield 190 mg, m.p. 117°–119° C.

Analysis %: Found: C, 45.2; H, 4.0; N, 13.4; Calculated for C₁₂H₁₃Cl₂N₃OS requires: C, 45.3; H, 4.1; N, 13.2.

EXAMPLE 18

The following compound, m.p. 88°–9°, was prepared similarly to the preceding Example from the appropriate thiol, methyl iodide, and K₂CO₃:

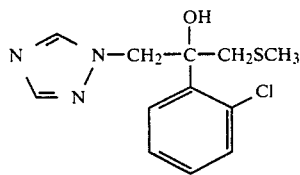

Analysis %: Found: C, 50.69; H, 4.87; N, 15.14; Calculated for $C_{12}H_{14}ClN_3OS$: C, 50.88; H, 4.95; N, 14.84.

EXAMPLE 19

Preparation of 3-Methylsulphonyl-2-(2,4-dichlorophenyl)-1-(1H-1,2,4-triazol-1-yl)propan-2-ol 3-Methylthio-2-(2,4-dichlorophenyl)-1-(1H-1,2,4-triazol-1-yl)propan-2-ol (150 mg) was dissolved in a mixture of isopropanol and chloroform (20 ml, 1:1, v/v) and metachloroperbenozic acid (MCPBA; 85%) (96 mg) added. The solution was stirred for three hours at room temperature (20° C.), then the solvent was removed at 50° C. under reduced pressure and replaced by chloroform (20 ml). This crude mixture of sulphoxides was then stirred for three hours with metachloroperbenzoic acid (200 mg) until only the sulphone was present by t.l.c. The chloroform solution was washed with dilute sodium metabisulphite solution (2×10 ml, 5%), potassium carbonate solution (2×10 ml, 5%), and dried (MgSO4). Evaporation gave a gum, which on trituration with ether gave a white solid, which was recrystallized from isopropanol to give colorless crystals of the title compound, yield 125 mg, m.p. 159°–161° C.

Analysis %: Found: C, 41.5; H, 3.7; N, 12.2; $C_{12}H_{13}Cl_2N_3O_3S$ requires: C, 41.2; H, 3.7; N, 12.0.

One step oxidation of the methylthio compound in chloroform with excess MCPBA also gave the title methylsulphonyl derivative, in slightly reduced yield.

EXAMPLE 20

The following compound was also prepared similarly to the Example 19 by oxidation of the corresponding thio compound (n=0) with MCPBA:

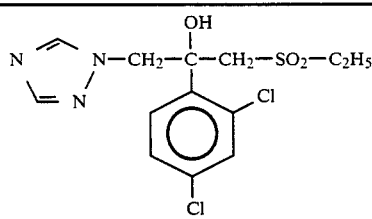

| m.p. (°C.) | Analysis % (Theoretical in brackets) | | |
|---|---|---|---|
| | C | H | N |
| 140–141° | 43.2 | 4.1 | 11.7 |
| | (42.9 | 4.2 | 11.5) |

EXAMPLE 21

The following compound, m.p. 100°–101°, was prepared similarly to Example 19 by the strong MCPBA oxidation of the corresponding methylthio compound:

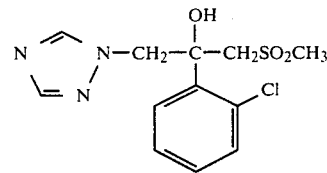

Analysis %: Found: C, 45.43; H, 4.49; N, 13.47; Calculated for $C_{12}H_{14}ClN_3O_3S$: C, 45.64; H, 4.44; N, 13.31.

EXAMPLE 22

The following compound, m.p. 195°–196.5°, was prepared similarly to Example 19 by the strong MCPBA oxidation of the corresponding methylthio compound, and was characterized as the methanesulphonic acid salt:

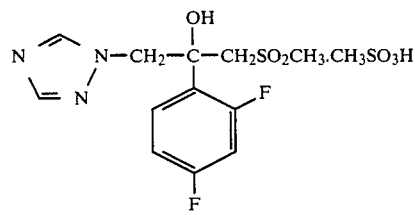

Analysis %: Found: C, 38.15; H, 4.11; N, 10.31; Calculated from $C_{12}H_{13}F_2N_3O_3S.CH_3SO_3H$: C, 37.77; H, 4.15; N, 10.16.

EXAMPLE 23

The following compound, m.p. 102°, was prepared similarly to Example 16, starting from the appropriate oxirane and thiolacetic acid, followed by deacylation using $C_2H_5ONa/C_2H_5OH/HCl$:

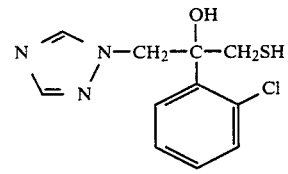

Analysis %: Found: C, 49.12; H, 4.49; N, 15.90; Calculated for $C_{11}H_{12}ClN_3OS$: C, 49.07; H, 4.46; N, 15.61.

EXAMPLE 24

Preparation of 3-Acetylthio-2-(2,4-Dichlorophenyl)-1-(1H-1,2,4-triazol-1-yl)propan-2-ol, and Its O-Acetyl Derivative (Dioxalate Salt)

2-(1H-1,2,4-triazol-1-ylmethyl)-2-(2,4-dichlorophenyl)oxirane (400 mg) was stirred overnight at room temperature with thioacetic acid (CH3COSH) (340 mg, 3 equivalents) and sodium hydride (75 mg of 50% dispersion in oil, 1 equivalent) in dry dimethylformamide (7 ml). The solution was diluted to 35 ml with water, adjusted to pH 9 with solid potassium carbonate, and extracted with ethyl acetate (3×20 ml). The combined organic extracts were washed with aqueous potassium carbonate solution (3×10 ml, 5%), dried (MgSO4) and evaporated to a gum. This gum was flash chromatographed on silica, eluting to give:

firstly (a) 160 mg of a gum, $R_f$ 0.5 (acetone: ether, 1:4). This formed a solid dioxalate salt, yield 136 mg, m.p. 90°–92°, when treated with anhydrous oxalic acid in ether. This salt was the dioxalate salt of the O-acetyl derivative of the title compound. It is believed that one mole of the oxalic acid was interstitial.

Analysis %: Found: C, 40.2; H, 3.4; N, 7.7; $C_{15}H_{15}Cl_2N_3O_3S.2(COOH)_2$ requires: C, 40.2; H, 3.4; N, 7.4.

and secondly (b) 60 mg of a gum, $R_f$ 0.4, which was recrystallized from diisopropyl ether, yield 45 mg, m.p. 124°–128°, of the title compound, 3-acetylthio-2-(2,4-dichlorophenyl)-1-(1H-1,2,4-triazol-1-yl)propan-2-ol.

Analysis %: Found: C, 45.1; H, 3.8; N, 12.1; $C_{13}H_{13}Cl_2N_3O_2S$ requires: C, 44.9; H, 3.8; N, 12.2.

The following Preparations illustrate the preparation of certain starting materials.

PREPARATION 1

(i) Preparation of 2-(1H-1,2,4-Triazol-1-yl)-2',4'-dichloroacetophenone (A)

This compound was prepared similarly to the method described in British Patent Specification No. 1,512,918:

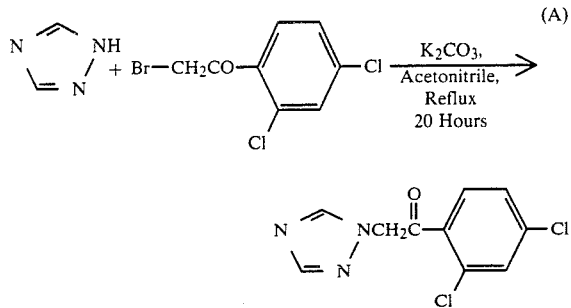

(ii) Preparation of 2-(2,4-Dichlorophenyl)-2-(1H-1,2,4-triazol-1-ylmethyl)oxirane (B)

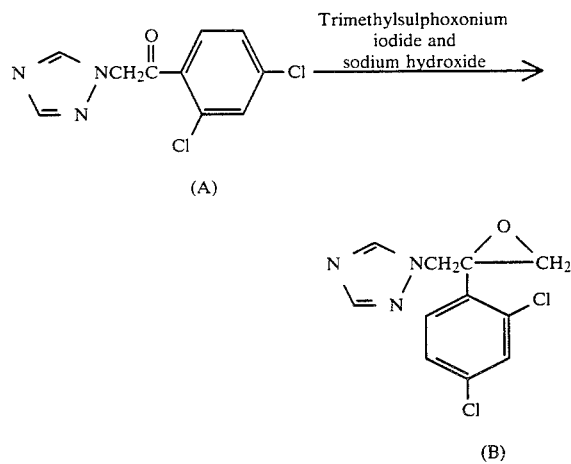

3.78 g (0.079 mole) of sodium hydride (50% dispersion in oil) was suspended, with stirring, in 20 ml of dry ether. The ether was then removed by decantation, and the sodium hydride was dried in a stream of dry nitrogen. 100 ml of dry dimethylsulphoxide was added followed by 17.34 g (0.079 mole) of dry powdered trimethylsulphoxonium iodide, in portions, over 15 minutes. The resulting mixture was stirred for 30 minutes at room temperature (20° C.). 18.33 g (0.072 mole) of compound (A) as a solution in 50 ml of dry dimethylsulphoxide was then added. The mixture was heated at 60° C. for three hours and then stood at room temperature overnight. The reaction mixture was cooled and quenched in ice. The product was then extracted into ethyl acetate (600 ml). The ethyl acetate layer was separated, dried over magnesium sulphate, and concentrated to give a red gum. Column chromatography of the gum on silica, eluting with ether, gave the product (B). On evaporation, 6.62 g (34.4%) of the title compound (B) was obtained as a gum which spontaneously crystallized (m.p. 56°–58° C.). N.m.r. (CDCl$_3$) was consistent with the desired structure. The oxirane (B) was then used directly.

PREPARATION 2

(i) Preparation of 2-Chloro-2',4'-Difluoroacetophenone

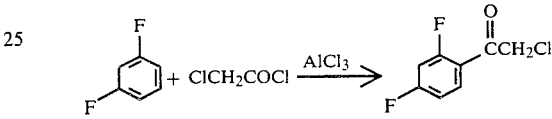

Chloroacetyl chloride (113 g, 1.0M) was added dropwise to a stirred mixture of 1,3-difluorobenzene (114 g, 1.0M) and anhydrous aluminum chloride (146.6 g, 1.1M) at room temperature (20° C.). The mixture was stirred for a further five hours at 50°–55° C. Methylene chloride (48.5 ml) was added slowly as the mixture was allowed to cool to room temperature. The methylene chloride layer was separated, washed with water (2×320 ml) and solvent removed by distillation at reduced pressure leaving a pale yellow solid (180 g).

A portion of the crude product (145 g) was crystallized from n-hexane (435 ml) giving the title compound (113 g, 73%), m.p. 47°–49° C. (literature* 46.5° C.). IR (KBr) and nmr (CDCl$_3$) were consistent with the desired structure.

*Von D. Ehlers, H. Bercher and A. Grisk, *J. Prakt. Chem.*, 315, 1169 (1973).

(ii) Preparation of 2',4'-Difluoro-2-(1H-1,2,4-triazol-1-yl)acetophenone hydrochloride

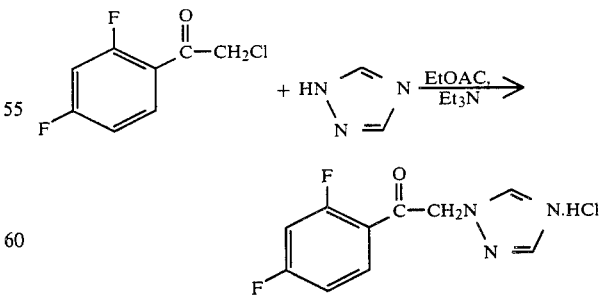

To a mixture of 1,2,4-triazole (30.4 g, 0.44M) and triethylamine (15.1 g, 0.15M) in refluxing ethyl acetate (186 ml) was added a solution of 2-chloro-2',4'-difluoroacetophenone (38.1 g, 0.2M) in ethyl acetate (80 ml). The mixture was refluxed for six hours then cooled to room temperature and the insolubles were removed by filtration. The filtrate was washed with water (2×200 ml) and then the solvent was removed by distillation at reduced pressure. The crude product was dissolved in ethyl acetate (150 ml) then 25% w/v HCl gas in isopropanol was added. The mixture was granulated at 0° C. for one hour and then the solid was collected by filtration and dried to give the title compound (21.6 g, 40%), m.p. 167°–170° C. IR (KBr) and nmr (DMSO) were consistent with the desired structure.

This intermediate was characterized as the free base, which was prepared by the following technique:

To a stirred slurry of sodium bicarbonate (16.8 g, 0.2M) and 1,2,4-triazole (27.6 g, 0.4M) in refluxing toluene (180 ml) was added a solution of 2-chloro-2',4'-difluoroacetophenone (38.1 g, 0.2M) in toluene (45 ml). The mixture was stirred at reflux for three hours and the water formed during the reaction was removed using a Dean and Stark trap. The reaction mixture was cooled to room temperature and then water (180 ml) was added. The toluene layer was separated and the solvent removed by distillation at reduced pressure. The resulting pale brown solid was crystallized from 1:1 ethyl acetate:n-hexane (70 ml) giving the title compound (3.9 g), m.p. 103°–105° C. The IR (KBr) and nmr (CDCl₃) were consistent with the desired structure.

Analysis %: Found: C, 53.62; H, 3.15; N, 18.68; Calculated for $C_{10}H_7F_2N_3O$: C, 53.8; H, 3.16; N, 18.82.

(iii) Preparation of 1-[2-(2,4-Difluorophenyl)-2,3-epoxypropyl]-1H-1,2,4-triazole methanesulphonate

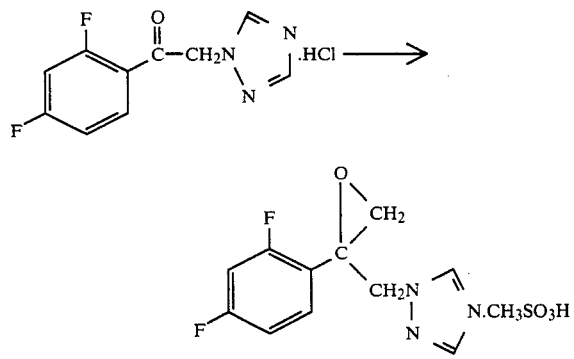

2',4'-Difluoro-2-(1H-1,2,4-triazol-1-yl)acetophenone hydrochloride (59.6 g, 0.23M), trimethylsulphoxonium iodide (50.6 g, 0.23M) and cetrimide (2.1 g) were stirred in a mixture of toluene (370 ml) and 20% w/w aqueous sodium hydroxide at 60° for 3 hours. The toluene layer was separated and concentrated to 110 ml then diluted with ethyl acetate (150 ml). A solution of methanesulphonic acid (16.6 g, 0.172M) in ethyl acetate (20 ml) was added. More ethyl acetate (100 ml) was added and the mixture was stirred at 0° C. for one hour then filtration of the precipitate gave the title compound (43 g, 56%).

20 g of the crude proudct was dissolved in hot industrial methylated spirits (140 ml) and carbon (2 g) was added. After stirring for 5 minutes, the mixture was filtered and the filtrate was concentrated to 100 ml then the mixture was stirred at 0° C. for one hour. Filtration gave the title compound (7.8 g, 39%), m.p. 128°–129° C. The IR (KBr) and nmr (DMSO) were consistent with the desired structure.

Analysis %: Found: C, 42.83; H, 3.92; N, 12.96; Calculated for $C_{12}H_{13}F_2N_3O_4S$: C, 43.2; H, 3.9; N, 12.6.

PREPARATION 3

The following oxirane, m.p. 47°–48°, was prepared similarly to the previous Preparation Part (iii) from corresponding starting materials:

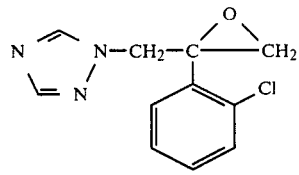

N.m.r. (CDCl₃), delta=8.0, (s), 1H; 7.83, (s), 1H; 7.2, (m), 4H; 4.88 (d), J15 Hz, 1H; 4.47, (d), J15 Hz, 1H; 2.90, (s), 2H.

Similarly, the ketone starting material needed to prepare this oxirane was prepared similarly to Part (ii) of the previous Preparation but using acetone as the solvent at room temperature.

The following PD₅₀ values were obtained for the compounds of this application. The test method used was as described in the text:

| Example No. | PD₅₀ (oral) v. *Candida albicans* (mice) PD₅₀ |
|---|---|
| 1 | 2.0 |
| 2 | 1.0 |
| 3 | 2.2 |
| 4 | 1.3 |
| 5A | 2.0 |
| 5B | 2.0 |
| 6 | 0.2 |
| 7 | 0.3 |
| 8 | 1.2 |
| 9 | 1.0 |
| 10 | 1.1 |
| 11 | 3.1 |
| 12 | 1.1 |
| 13 | 2.2 |
| 14 | 1.3 |
| 15 | 0.8 |
| 16 | 0.5 |
| 17* | 0.2 |
| 18 | 2.3 |
| 19 | 0.2 |
| 20 | 0.8 |
| 21 | 4.2 |
| 22 | 3.1 |
| 23 | 6.4 |
| 24 | 0.6 |

*The analogous oxyether, —OCH₃, in place of —SCH₃ is inactive at 10 mg/kg. Its PD₅₀ is, therefore, >10.

We claim:
1. Compounds of the formula

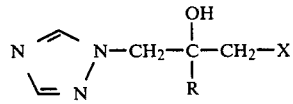

wherein
R is mono- or disubstituted phenyl wherein the substituent is Cl or F;
X is SH, S(C₂–C₄ alkanoyl), SO₂(C₁–C₃ alkyl) or S(O)ₙR¹ wherein R¹ is C₁–C₆ alkyl, C₃–C₇ cycloalkyl, or C₁–C₂ alkyl substituted by C₂–C₄ alkenyl;
n is 0 or 1;

and their pharmaceutically acceptable salts.

2. The compound according to claim 1 wherein R is 2,4-dichlorophenyl, $R^1$ is $CH_3$ and n is 1.

3. The compound according to claim 1 wherein R is 2,4-dichlorophenyl, $R^1$ is $CH_3$ and n is 0.

4. A pharmaceutical composition comprising a compound as claimed in claim 1 together with a pharmaceutically acceptable diluent or carrier.

5. A method of treating a fungal infection in a human being, which comprises administering to said human an antifungal amount of a compound as claimed in claim 1.

6. A compound according to claim 1 wherein X is $SO_2(C_1-C_3$ alkyl) and R is 2,4-dichlorophenyl.

7. The compound according to claim 2 wherein X is $SO_2CH_3$.

8. The compound according to claim 1 wherein R is 2,4-dichlorophenyl and X is $S(C_2$ alkanoyl).

9. The compound according to claim 1 wherein R is 2,4-dichlorophenyl and X is SH.

* * * * *

Adverse Decision in Interference

In Interference No. 102,243, involving Patent No. 4,661,507 G. E. Gymer, K. Richardson, ANTIFUNGAL S-ETHERS OF 2-ARYL-3-MERCAPTO-1-(1H-1, 2, 4- TRIAZOL-YL) PROPAN-2-OLS AND CORRESPONDING SULFOXIDES AND SULFONES, final judgment asverse to the patentees was rendered June 13, 1990, as to claims 1-9.

*[Official Gazette August 28, 1990]*